United States Patent
Wiederhold et al.

(10) Patent No.: US 10,214,471 B2
(45) Date of Patent: Feb. 26, 2019

(54) METHOD FOR PRODUCING PROPYLENE GLYCOL FROM PROPENE AND HYDROGEN PEROXIDE

(71) Applicant: EVONIK DEGUSSA GMBH, Essen (DE)

(72) Inventors: Holger Wiederhold, Darmstadt (DE); David Bolz, Frankfurt (DE); Bernd Jaeger, Bickenbach (DE); Hans-Jürgen Köhle, Mainhausen (DE); Sebastian Imm, Bad Vilbel (DE); Georg Friedrich Thiele, Friedberg (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/778,562

(22) PCT Filed: Nov. 1, 2016

(86) PCT No.: PCT/EP2016/076270
§ 371 (c)(1),
(2) Date: May 23, 2018

(87) PCT Pub. No.: WO2017/089075
PCT Pub. Date: Jun. 1, 2017

(65) Prior Publication Data
US 2018/0354878 A1 Dec. 13, 2018

(30) Foreign Application Priority Data

Nov. 25, 2015 (EP) .................................... 15196268

(51) Int. Cl.
| C07C 29/48 | (2006.01) |
| C07C 29/80 | (2006.01) |
| C07C 29/76 | (2006.01) |

(52) U.S. Cl.
CPC .............. *C07C 29/48* (2013.01); *C07C 29/76* (2013.01)

(58) Field of Classification Search
CPC ................................ C07C 29/48; C07C 29/76
See application file for complete search history.

(56) References Cited

U.S. PATENT DOCUMENTS

| 4,308,409 | A  | 12/1981 | Wu et al. |
| 5,274,140 | A  | 12/1993 | Venturello et al. |
| 6,372,924 | B2 | 4/2002  | Thiele |
| 6,673,950 | B1 | 1/2004  | Teles et al. |
| 6,861,042 | B2 | 3/2005  | Korl et al. |
| 7,601,263 | B2 | 10/2009 | Ebert et al. |
| 7,658,893 | B2 | 2/2010  | Bassler et al. |
| 7,670,572 | B2 | 3/2010  | Porscha et al. |
| 7,833,498 | B2 | 11/2010 | Goebbel et al. |
| 7,863,211 | B2 | 1/2011  | Strebelle et al. |
| 8,545,673 | B2 | 10/2013 | Dietz et al. |
| 9,539,549 | B2 | 1/2017  | Haensel et al. |
| 10,100,024 | B2 | 10/2018 | Stochinol et al. |
| 10,125,108 | B2 | 11/2018 | Jahn et al. |
| 2003/0040637 | A1 | 2/2003 | Hofen et al. |
| 2006/0058539 | A1 | 3/2006 | Babler et al. |
| 2015/0007951 | A1 | 1/2015 | Dietz et al. |
| 2017/0210718 | A1 | 7/2017 | Stochinol et al. |
| 2018/0002299 | A1 | 1/2018 | Bolz et al. |
| 2018/0002300 | A1 | 1/2018 | Bolz et al. |
| 2018/0030010 | A1 | 2/2018 | Breitenbach et al. |
| 2018/0030011 | A1 | 2/2018 | Stock et al. |
| 2018/0030012 | A1 | 2/2018 | Stock et al. |
| 2018/0057473 | A1 | 3/2018 | Stock et al. |
| 2018/0134676 | A1 | 5/2018 | Jahn et al. |

FOREIGN PATENT DOCUMENTS

| DE | 195 07 584 | 9/1996 |
| EP | 0 100 119 | 2/1984 |
| EP | 0 230 949 | 8/1987 |
| EP | 0 659 473 | 6/1995 |
| EP | 0 757 045 | 2/1997 |
| EP | 1 247 806 | 10/2002 |
| EP | 1 489 074 | 12/2004 |
| WO | WO 02/085873 | 10/2002 |
| WO | WO 03/016296 | 2/2003 |
| WO | WO 03/018567 | 3/2003 |
| WO | WO 03/093255 | 11/2003 |
| WO | WO 2004/018088 | 3/2004 |
| WO | WO 2004/048335 | 6/2004 |
| WO | WO 2004/048354 | 6/2004 |
| WO | WO 2004/048355 | 6/2004 |

(Continued)

OTHER PUBLICATIONS

International Search Report for PCT/EP2016/076270 filed Nov. 1, 2016.
Written Opinion of the International Searching Authority for PCT/EP2016/076270 filed Nov. 1, 2016.
International Preliminary Report on Patentability for PCT/EP2016/076270 filed Nov. 1, 2016.
Chowdhury, et al, "Recovery of Homogeneous Polyoxometallate Catalysts from Aqueous and Organic Media by a Mesoporous Ceramic Membrane without Loss of Catalytic Activity," *Chem. Eur. J.* 12(11):3061-3066 (Apr. 2006).

(Continued)

Primary Examiner — Sikarl A Witherspoon
(74) Attorney, Agent, or Firm — Michael A. Sanzo, LLC (57) ABSTRACT

The process for preparing 1,2-propanediol from propene and hydrogen peroxide comprises the steps of
a) reacting propene with hydrogen peroxide in the presence of a catalyst mixture comprising a phase transfer catalyst and a heteropolytungstate, wherein the reaction is carried out in a liquid mixture comprising an aqueous phase having a pH of at most 6 and an organic phase,
b) separating the biphasic mixture from step a) into an aqueous phase and an organic phase comprising propene oxide,
c) recycling the propene oxide present in the separated organic phase into the reaction of step a) and
d) separating 1,2-propanediol from the aqueous phase separated in step b).

22 Claims, 4 Drawing Sheets

(56) References Cited

FOREIGN PATENT DOCUMENTS

| WO | WO 2005/000827 | 1/2005 |
|---|---|---|
| WO | WO 2005/103024 | 11/2005 |
| WO | WO 2008/141734 | 11/2008 |
| WO | WO 2011/063937 | 6/2011 |

OTHER PUBLICATIONS

Guojie, et al., "Factors Affecting Propylene Epoxidation Catalyzed by Reaction-Controlled Phase-Transfer Catalyst," *Chinese Journal of Catalysis* 26:1005-1010 (Nov. 2005).

Kaur, et al., "Poloxometalate-catalysed epoxidation of propylene with hydrogen peroxide: microemulsion versus biphasic process," *Catalysis Communications* 5(11): 709-713 (Nov. 2004).

Li, et al., "Influence of composition of heteropolyphophatotungstate catalyst on epoxidation of propylene," *Journal of Molecular Catalysis A: Chemical* 218(2):247-252 (Aug. (2004).

Luthra, et al., "Homogeneous phase transfer catalyst recovery and re-use using solvent resistant membranes," *Journal of Membrane Science* 201:65-75 (2002).

Venturello, et al., "A New, Effective Catalytic System for Epoxidation of Olefins by Hydrogen Peroxide under Phase-Transfer Conditions," *J. Org. Chem.* 483831-3833 (1983).

U.S. Appl. No. 15/329,626, filed Jan. 26, 2017, US-2017/0210718 A1, Jul. 27, 2017, Stochinol.

U.S. Appl. No. 15/570,167, filed Oct. 15, 2017, US-2018/0134676 A1, May 27, 2018, Jahn.

U.S. Appl. No. 15/778,318, filed May 23, 2018, Brendel.

U.S. Appl. No. 15/778,337, filed May 23, 2018, Pascaly.

U.S. Appl. No. 15/778,425, filed May 23, 2018, Hofen.

U.S. Appl. No. 16/070,873, filed Jul. 18, 2018, Schmidt.

Notice of Allowance dated Oct. 16, 2018 for copending U.S. Appl. No. 15/778,318.

METHOD FOR PRODUCING PROPYLENE GLYCOL FROM PROPENE AND HYDROGEN PEROXIDE

CROSS REFERENCE TO RELATED APPLICATIONS

The present application is US national stage of international application PCT/EP2016/076270, which had an international filing date of Nov. 1, 2016, and which was published on Jun. 1, 2017. Priority is claimed to European application EP 15196268.5, filed on Nov. 25, 2015.

The invention relates to a process for preparing 1,2-propanediol from propene and hydrogen peroxide which does not require isolation and purification of propene oxide.

1,2-Propanediol is prepared industrially by reacting propene oxide with water. Propene oxide is prepared industrially by epoxidation of propene. In the established process, propene oxide is isolated from the reaction mixture of the epoxidation and purified before it is converted to 1,2-propanediol.

In the course of preparation of propene oxide by the HPPO process, in which propene and hydrogen peroxide are reacted in the presence of a titanium silicalite in methanol as solvent, 1,2-propanediol and 1,2-propanediol monomethyl ether are obtained as by-products.

WO 04/009568 proposes producing a crude propene oxide having a content of 95 to 99%, by distillation from the reaction mixture of the HPPO process, this being reacted with water without further purification to give 1,2-propanediol and to purify 1,2-propanediol together with by-product separated from the bottom product of the distillation. Also in this process, propene oxide is isolated and converted to 1,2-propanediol in a separate reactor.

J. Guojie et al. in Chinese Journal of Catalysis 26 (2005) 1005-1010 describe the epoxidation of propene with hydrogen peroxide in the presence of a quaternary ammonium heteropolyphosphatotungstate as catalyst in a biphasic reaction mixture with CHCl3 or a mixture of toluene and tributyl phosphate as solvent. To improve the selectivity for propene oxide, $K_2HPO_4$ or $Na_2HPO_4$ are added as additive. Without addition of an additive, more 1,2-propanediol than propene oxide is obtained with selectivities for 1,2-propanediol of 41.2 and 56.3%.

J. Kaur et al. in Catal. Commun. 5 (2004) 709-713 describe the epoxidation of propene with hydrogen peroxide in the presence of methyltrioctylammonium peroxopolytungstate. The epoxidation is carried out either in a microemulsion produced by adding the surfactant Brij® 30 or in a biphasic system with 1,2-dichloroethane as solvent. For the biphasic system, for reuse of the catalyst, the phases are separated, the organic phase is extracted with water and propene oxide and unreacted propene are removed by purging with nitrogen at 60° C. For the microemulsion, a membrane ultrafiltration is proposed for separating catalyst and water in order to reuse the catalyst.

S. R. Chowdhury et al., Chem. Eur. J. 12 (2006) 3061-3066 describe an epoxidation of cyclooctene with hydrogen peroxide in the presence of $[CH_3N(C_8H_{17})_3]_{12}[WZn_3(ZnW_9O_{34})_2]$ as catalyst and toluene as solvent with removal of the catalyst by filtration over alumina membranes having average pore radii of 2.3 nm and 4.3 nm. Using the alumina membrane having an average pore radius of 2.3 nm, $Na_{12}[WZn_3(ZnW_9O_{34})_2]$ was also removed from an aqueous solution.

S. S. Luthra et al., J. Membr. Sci. 201 (2002) 65-75 describe the separation of the phase transfer catalysts tetra-n-butylammonium bromide and tetra-n-octylammonium bromide from toluene by nanofiltration.

It has now been found that propene can be reacted with hydrogen peroxide in high yields and selectivities in one stage to give 1,2-propanediol if the reaction is carried out using a combination of a phase transfer catalyst and a heteropolytungstate in a reaction mixture having two liquid phases, in which the pH of the aqueous phase is maintained below 6, the propene oxide present in the organic phase of the reaction mixture is recycled into the reactor and 1,2-propanediol is separated from the aqueous phase.

Accordingly, the invention relates to a process for preparing 1,2-propanediol from propene and hydrogen peroxide comprising the steps of
a) reacting propene with hydrogen peroxide in the presence of a catalyst mixture comprising a phase transfer catalyst and a heteropolytungstate, wherein the reaction is carried out in a liquid mixture comprising an aqueous phase having a pH of at most 6 and an organic phase,
b) separating the biphasic mixture from step a) into an aqueous phase P1 and an organic phase P2,
c) recycling the propene oxide present in the separated organic phase P2 into the reaction of step a) and
d) separating 1,2-propanediol from the aqueous phase P1 separated in step b).

In the process according to the invention, propene is reacted with hydrogen peroxide in step a) in the presence of a catalyst mixture comprising a phase transfer catalyst and a heteropolytungstate. The reaction is carried out in a liquid mixture comprising two liquid phases, an aqueous phase and an organic phase.

Propene can be used in pure form or in a mixture with propane, wherein the proportion of propane may be up to 20 mol %. The proportion of propane in the propene used is preferably less than 5 mol %.

Hydrogen peroxide is preferably used in the form of an aqueous solution, preferably with a hydrogen peroxide content of 10 to 80% by weight, particularly preferably 30 to 70% by weight. In the process according to the invention, the hydrogen peroxide crude product is obtained in the extraction stage of the anthraquinone process for producing hydrogen peroxide may be used.

The aqueous phase comprises water, unreacted hydrogen peroxide and 1,2-propanediol formed. The organic phase comprises propene, and propene oxide formed as intermediate and can in addition comprise propane originating from the propene used. In addition, the organic phase may comprise at least one solvent immiscible with water.

The catalyst mixture used in the process according to the invention comprises a heteropolytungstate, wherein the heteroatom is preferably phosphorus or arsenic and is particularly preferably phosphorus, i.e. the heteropolytungstate is particularly preferably a polytungstophosphate. Heteropolytungstates are known from the prior art to those skilled in the art. Special preference is given to polytungstophosphates having a molar ratio of phosphorus to tungsten in the range of from 1:2 to 1:12. Polytungstophosphate is preferably generated in situ in the liquid mixture in step a) from phosphoric acid and sodium tungstate, wherein phosphoric acid and sodium tungstate are preferably used at a molar ratio of phosphorus to tungsten in the range of from 1:2 to 10:1 and particularly of from 4:1 to 8:1. Peroxotungstates and peroxotungstophosphates, for example $PO_4[WO(O_2)_2]_4^{3-}$ and $HPO_4[WO(O_2)_2]_2^{2-}$ and also partially protonated forms thereof, are formed from a polytungstophosphate with hydrogen peroxide in the aqueous phase.

The catalyst mixture used in the process according to the invention also comprises a phase transfer catalyst. The phase transfer catalyst comprises a cation or a compound which forms a cation in the aqueous phase, wherein the cation can form an organic phase soluble salt with a peroxotungstate or heteropolyperoxotungstate. The phase transfer catalyst preferably comprises a singly-charged cation or a compound which forms a singly-charged cation in the aqueous phase. Suitable as phase transfer catalyst are quaternary ammonium salts, tertiary amines or quaternary phosphonium salts. Suitable quaternary ammonium salts are tetraalkylammonium salts having in total at least 12 carbon atoms in the alkyl groups, for example dodecyltrimethylammonium salts, hexadecyltrimethylammonium salts, octadecyltrimethylammonium salts, methyltributylammonium salts and methyltrioctylammonium salts. Quaternary ammonium salts with mono- or divalent anions are suitable, for example chloride, bromide, nitrate, sulphate, hydrogenphosphate, dihydrogenphosphate, methylsulphonate, methylsulphate and ethylsulphate. Suitable tertiary amines are dodecyldimethylamine, hexadecyldimethylamine, octadecyldimethylamine, tributylamine and trioctylamine. The phase transfer catalyst is preferably used in an amount which results in a molar ratio in the liquid mixture of phase transfer catalyst to tungsten in the range of from 0.2:1 to 3:1 and particularly preferably of from 0.4:1 to 1:1, wherein the molar ratio refers to the cations or compounds forming cations contained in the phase transfer catalyst used and to the amount of tungsten used.

In a preferred embodiment, the phase transfer catalyst comprises at least one salt having a tertiary or quaternary ammonium ion of the structure $R^1R^2R^3R^4N^+$, where $R^1$ is a $Y—O(C=O)R^5$ group, where Y is one of the groups $CH_2CH_2$, $CH(CH_3)CH_2$ and $CH_2CH(CH_3)$ and $R^5$ is an alkyl group or alkenyl group having 11 to 21 carbon atoms, $R^2$ is hydrogen or an alkyl group having 1 to 4 carbon atoms, and
$R^3$ and $R^4$ are each independently $R^1$, an alkyl group having 1 to 4 carbon atoms or Y—OH.

Preference is given to quaternary ammonium salts having methylsulphate as anion, in which $R^2$ is a methyl group and $R^5$ is a linear alkyl group or alkenyl group. Particular preference is given to the salts $(CH_3)_3N^+CH_2CH_2O(C=O)R^5CH_3OSO_3^-$, $(CH_3)_2N^+(CH_2CH_2OH)(CH_2CH_2O(C=O)R^5)$ $CH_3OSO_3^-$, $(CH_3)_2N^+(CH_2CH_2O(C=O)R^5)_2$ $CH_3OSO_3^-$, $CH_3N^+(CH_2CH_2OH)_2(CH_2CH_2O(C=O)R^5)$ $CH_3OSO_3^-$, $CH_3N^+(CH_2CH_2OH)(CH_2CH_2O(C=O)R^5)_2$ $CH_3OSO_3^-$, $CH_3N^+(CH_2CH_2O(C=O)R^5)_3$ $CH_3OSO_3^-$, $(CH_3)_3N^+CH_2CH(CH_3)O(C=O)R^5$ $CH_3OSO_3^-$, $(CH_3)_2N^+(CH_2CH(CH_3)OH)(CH_2CH(CH_3)O(C=O)R^5)$ $CH_3OSO_3^-$ and $(CH_3)_2N^+(CH_2CH(CH_3)O(C=O)R^5)_2CH_3OSO_3^-$, in which $R^5$ is in each case a linear alkyl group or alkenyl group having 11 to 21 carbon atoms. Special preference is given to the salt $(CH_3)_2N^+(CH_2CH(CH_3)O(C=O)R^5)_2$ $CH_3OSO_3^-$ in which $R^5$ is an alkyl group or alkenyl group having 11 to 17 carbon atoms. The phase transfer catalysts of this embodiment may be prepared by esterifying ethanolamine, isopropanolamine, diethanolamine, diisopropanolamine, triethanolamine or triisopropanolamine with a fatty acid and subsequent quaternization with dimethyl sulphate and have the advantage, compared to tetraalkylammonium salts, that they are readily biodegradable and the waste water resulting from the process according to the invention can be introduced into a biological treatment plant without further pretreatment. Using the preferred salts with methylsulphate as anion, the corrosivity of the reaction mixture can also be reduced in comparison to tetraalkylammonium halides. In this embodiment, preferably the phase transfer catalyst mixed with at least one solvent selected from ethanol and 2-propanol is added to the liquid mixture of the reaction. By using this solvent, the phase transfer catalyst can be more easily dosed and distributed in the liquid mixture.

The phase transfer catalyst and the heteropolytungstate can be fed to the reaction as a mixture or separately from each other. Phase transfer catalyst and heteropolytungstate are preferably fed separately in step a).

The reaction of propene with hydrogen peroxide is carried out at a pH of the aqueous phase of at most 6. The pH of the aqueous phase is preferably maintained in the range from 1.0 to 3.5, particularly preferably in the range from 2.0 to 3.0. The pH can be maintained in this range by addition of acid, preferably sulphuric acid or phosphoric acid, or by addition of base, preferably aqueous sodium hydroxide solution. The term pH here refers to the apparent pH measured with a glass electrode, wherein the glass electrode has been calibrated with aqueous buffer solutions. By adjusting to a pH in the preferred range, high selectivity for 1,2-propanediol can be achieved and enrichment of propene oxide in the aqueous phase can be prevented, which simplifies the subsequent separation of 1,2-propanediol from the aqueous phase.

The reaction of propene with hydrogen peroxide is preferably carried out with a molar excess of propene, wherein propene is preferably used in a molar ratio of propene to hydrogen peroxide of from 1.1:1 to 10:1.

The reaction is carried out preferably at a temperature in the range of 30 to 100° C., particularly preferably 70 to 90° C. The reaction is carried out preferably at a pressure which is higher than the saturated vapour pressure of propene at the temperature of the reaction such that the major portion of the propene is present in the organic phase of the liquid mixture.

The reaction of propene with hydrogen peroxide can be carried out with or without addition of solvents. The reaction is preferably carried out in the presence of at least one solvent having a boiling point of more than 100° C., preferably more than 120° C., and a water solubility at 20° C. of less than 250 mg/kg. The solvents used may be alcohols having one or more hydroxyl groups, ethers, esters, ketones or alkylated aromatic hydrocarbons. By using a solvent, the proportion of heteropolytungstate in the organic phase can be increased. The proportion of solvent is preferably selected such that the proportion of solvent in the organic phase during the reaction is in the range of 10 to 90% by weight.

In a particularly preferred embodiment, the solvent comprises an epoxidized fatty acid methyl ester. For this purpose, in place of the epoxidized fatty acid methyl ester, the corresponding fatty acid methyl ester with unsaturated fatty acid groups can also be used, which is converted to the epoxidized fatty acid methyl ester in the liquid mixture of step a). Most preferred are epoxidized fatty acid methyl esters whose fatty acid groups originate from vegetable oils, particularly soybean oil. The epoxidized fatty acid methyl esters have the advantage that they are poorly soluble in the aqueous phase and no separation of solvent from the aqueous phase of the reaction is required.

In a further preferred embodiment, the solvent comprises an alkylated aromatic hydrocarbon having 8 to 12 carbon atoms. Suitable alkylated aromatic hydrocarbons are, for example, 1,2-dimethylbenzene (o-xylene), 1,3-dimethylbenzene (m-xylene), 1,4-dimethylbenzene (p-xylene), ethylbenzene, 1,2,3-trimethylbenzene, 1,2,4-trimethylbenzene, 1,3,5-trimethylbenzene (mesitylene), 1-ethyl-2-methylbenzene, 1-ethyl-3-methylbenzene and 1-ethyl-4-methylbenzene and n-propylbenzene. Preferably hydrocarbon mixtures comprising more than 50% by weight, particularly preferably more than 80% by weight, alkylated aromatic hydrocarbons having 8 to 12 carbon atoms are used as solvent. By using a solvent comprising alkylated aromatic hydrocarbon having 8 to 12 carbon atoms, an extensive extraction of the heteropolytungstate into the organic phase of the reaction mixture can be achieved so that an improved recycling of the heteropolytungstate with the organic phase and a simplified recovery of heteropolytungstate from the organic phase of the reaction of propene with hydrogen peroxide can be achieved.

The phase transfer catalyst, the molar ratio of phase transfer catalyst to heteropolytungstate, the molar ratio of heteroatom of the heteropolytungstate to tungsten, the molar ratio of propene to hydrogen peroxide and type and amount of solvent optionally used are preferably selected such that as large a portion as possible of the tungsten present in the liquid mixture is transferred into the organic phase of the liquid mixture by the phase transfer catalyst. For this purpose, one of the aforementioned phase transfer catalysts based on an alkanolamine fatty acid ester is preferably used in combination with an epoxidized fatty acid methyl ester or a hydrocarbon mixture with more than 50% by weight alkylated aromatic hydrocarbons having 8 to 12 carbon atoms as solvent.

The reaction of propene with hydrogen peroxide may be carried out in batch or continuously, wherein a continuous reaction is preferred. In a continuous reaction, the concentration of hydrogen peroxide in the aqueous phase is preferably in the range of 0.1 to 5% by weight, particularly preferably 0.5 to 3% by weight. Such a concentration of hydrogen peroxide may be adjusted by the selection of the reaction temperature, the molar ratio of propene to hydrogen peroxide and the residence time of the liquid mixture in the reactor in which the reaction takes place.

During the reaction, the liquid mixture is preferably mixed in order to generate a large phase interface between the aqueous phase and the organic phase. For this purpose, the reaction is preferably carried out continuously in a loop reactor having fixed internals, and the liquid mixture is conducted through the loop reactor at a flow rate which generates a turbulent flow over the internals. Baffles, static mixing elements, structured packings or random packings can be used as internals for this purpose. Alternatively or in combination to this, the internals used may be heat exchangers, such as plate heat exchangers or tube bundle heat exchangers, in which turbulent flow is generated between the plates or in the tubes of the tube bundles.

In step b) of the process according to the invention, the biphasic mixture from step a) is separated into an aqueous phase P1 and an organic phase P2. The separation is preferably carried out in a settler vessel, and the biphasic mixture can be passed over a coalescer element comprising a structured packing or random packing with a surface wetted by the phase present dispersed in the biphasic mixture, in order to assist the separation.

The liquid phase is separated in step b) preferably in the presence of a gas phase. The reaction in step a) can lead to a decomposition of hydrogen peroxide with formation of oxygen and in step b) the gas phase may then comprise oxygen. In order to avoid the formation of a flammable gas phase, the oxygen content of this gas phase is therefore maintained below 7% by volume in step b), preferably by supplying inert gas and withdrawing a gas stream. The inert gas used may be nitrogen, argon, carbon dioxide or methane, wherein nitrogen is preferred.

In step c) of the process according to the invention, the propene oxide present in the organic phase P2 is recycled into the reaction of step a), in order to achieve as far as possible complete conversion of propene to 1,2-propanediol. Preferably, the heteropolytungstate present in the organic phase P2 is additionally recycled into the reaction of step a), the portion of the catalyst mixture present in the organic phase being particularly preferably substantially completely recycled into step a). Likewise, the propene present in the organic phase P2 is preferably recycled into the reaction of step a). If propene is used as a mixture with propane, the same amount of propane is preferably separated from the organic phase P2 in the recycling into step a), which is fed to step a) with the mixture of propene with propane. This way, enrichment of propane in the organic phase in step a) can be avoided when the reaction in step a) is performed continuously.

In a preferred embodiment of the process according to the invention, the organic phase P2 (9) separated in step b) is completely or partly recycled into the reaction of step a).

In a further preferred embodiment of the process according to the invention, the organic phase P2 is separated completely or partly by nanofiltration in step c) into a retentate enriched in heteropolytungstate and a permeate depleted in heteropolytungstate and the retentate is recycled into the reaction of step a). Preferably, the entire organic phase P2 is separated by nanofiltration into a retentate and a permeate. Corresponding to the nomenclature recommendation of the IUPAC, the term nanofiltration here refers to a pressure-driven separation at a membrane, in which the membrane retains particles and dissolved molecules having a diameter of less than 2 nm. For the nanofiltration in step c), a nanofiltration membrane is used which retains the salt of peroxotungstate or heteroperoxotungstate and the cation of the phase transfer catalyst in the retentate and allows propene to pass through with the permeate. The nanofiltration is then preferably operated such that the concentration of the salt of peroxotungstate or heteropolyperoxotungstate and the cation of the phase transfer catalyst in the retentate does not increase above the saturation concentration. Membranes based on the polymers polyimide, polyether sulphone, polyamide and polidimethylsiloxane can be used for the nanofiltration. Suitable nanofiltration membranes are commercially available, for example, from Evonik Membrane Extraction Technology MET under the name PuraMem® S600, from GMT Membrantechnik under the name ONF-2, from SolSep under the designations 010306, 030306, 030705 and 030306F, and from AMS Technologies under the name NanoPro™ SX. Preference is given to using one of the composite membranes known from DE 195 07 584, EP 1 741 481 and WO 2011/067054

The nanofiltration preferably takes place as a cross-flow filtration, preferably at a temperature in the range of 20 to 90° C., particularly preferably 40 to 80° C. The transmembrane pressure is preferably 2 to 5 MPa. The pressure on the retentate side can be up to 10 MPa. The pressure on the permeate side is preferably selected to be higher than the lowest pressure in steps a) and b) of the process in order to prevent outgassing of dissolved components on the permeate side.

In a likewise preferred embodiment, the organic phase P2 is separated by nanofiltration into a retentate enriched in heteropolytungstate and a permeate depleted in heteropolytungstate, a stream S1 comprising unreacted propene and propene oxide formed as intermediate is separated by distillation from the permeate and this stream is recycled into the reaction of step a). The distillation is preferably carried out at a pressure at which propene can be condensed with the distillate by cooling with water. Alternatively, the distillation may also be carried out at a lower pressure, propene oxide and only a portion of the propene can be condensed with the distillate and the remaining vapour can be compressed to condense the propene. In this embodiment, high-boiling by-products and degradation products of the phase transfer catalyst can be discharged with the bottom product of the distillation, and enrichment of poorly water-soluble by-products and impurities in the organic phase are avoided in step a) when the reaction in step a) is performed continuously. Removing stream S1 by distillation after the nanofiltration prevents further reaction of propene oxide, formed as intermediate, with the catalyst system by heating, which leads to by-products. If in step a) of the process the reaction is carried out in the presence of a solvent, it is preferred that, subsequent to the distillation for separating stream S1, the bottom product of this distillation is fed to a further distillation in which the solvent is separated by distillation. The solvent separated can be recycled into step a). If propene is used as a mixture with propane, the distillation is preferably carried out so that, in addition to stream S1, a further stream is obtained, consisting essentially of propene and propane, from which propene oxide is separated. Propane is completely or partly separated from this further stream and the resulting propene obtained, separated from propane or depleted in propane, is preferably recycled into step a). In this case, preferably the same amount of propane is removed, which is fed to step a) with the mixture of propene and propane. The distillation of the permeate may be carried out in two stages for this purpose, where in the first distillation stage, the further stream consisting largely of propene and propane is separated, and subsequently stream S1 is separated in the second distillation stage. The distillation however is preferably carried out in only one column with a side draw, stream S1 being removed as a side stream and the further stream consisting essentially of propene and propane being removed as overhead product of the column.

In a further preferred embodiment, the organic phase P2 is separated by distillation into a stream S1, comprising unreacted propene and propene oxide formed as intermediate, and a stream S2, depleted in propene and propene oxide, the stream S2 is separated by nanofiltration into a retentate enriched in heteropolytungstate and a permeate depleted in heteropolytungstate and the stream S1 is recycled into the reaction of step a). This embodiment is preferably used if the reaction in step a) of the process is carried out in the presence of a solvent and the distillation is then carried out such that the solvent remains in stream S2. The solvent can then be removed from the permeate of the nanofiltration, preferably by distillation, and can then be recycled into the reaction of step a). Compared to the embodiment described above, the embodiment with a separation of stream S1 prior to the nanofiltration has the advantage that a considerably smaller stream is separated by the nanofiltration, which reduces the apparatus size and the energy consumption of the nanofiltration. If propene is used as a mixture with propane, in this embodiment preferably a further stream is separated from stream S1 by an additional distillation, which consists essentially of propene and propane and from which propene oxide is separated, before stream S1 is recycled into step a). Propane is completely or partly separated from this further stream and the resulting propene obtained, separated from propane or depleted in propane, is preferably recycled into step a). In this case, preferably the same amount of propane is separated which is fed to step a) with the mixture of propene and propane.

In step d) of the process according to the invention, 1,2-propanediol is separated from the aqueous phase P1 separated in step b). The 1,2-propanediol can be separated from the aqueous phase by distillation, preferably by a two-stage distillation, in which water is distilled off in the first stage and 1,2-propanediol is distilled off in the second stage from the bottom product of the first stage.

Prior to the separation of 1,2-propanediol, peroxides are preferably removed by a catalytic hydrogenation. The hydrogenation is preferably carried out using a supported hydrogenation catalyst comprising one or more metals from the group of Ru, Rh, Pd, Pt, Ag, Ir, Fe, Cu, Ni and Co on a support, wherein activated carbon, $SiO_2$, $TiO_2$, $ZrO_2$, $Al_2O_3$ and aluminium silicates are preferred as support. Preference is given to hydrogenation catalysts comprising ruthenium as active metal. The catalytic hydrogenation is preferably carried out at a partial hydrogen pressure of 5 to 300 bar and a temperature of 80° C. to 180° C., preferably 90° C. to 150° C. The hydrogenation catalyst may be used as a suspension or as a fixed bed, a trickle bed hydrogenation with a fixed bed catalyst being preferred. The hydrogenation can prevent problems due to decomposition of hydrogen peroxide in a separation of 1,2-propanediol by distillation and reduce the by-products 1-hydroperoxy-2-propanol, 2-hydroperoxy-1-propanol and hydroxyacetone formed in step a) to 1,2-propanediol, and can thereby improve the yield of 1,2-propanediol.

In step d) of the process according to the invention, the aqueous phase P1 is preferably separated by nanofiltration into a retentate enriched in heteropolytungstate and a permeate depleted in heteropolytungstate, the retentate is recycled into the reaction in step a) and 1,2-propanediol is separated from the permeate. For the nanofiltration in step d), a nanofiltration membrane is used which retains peroxotungstate and heteropolyperoxotungstate in the retentate and allows water and 1,2-propanediol to pass through with the permeate. The nanofiltration is operated so that the solubility limit of the heteropolytungstate in the retentate is not exceeded. For a continuous reaction in step a), preferably that much water is recycled to step a) with the retentate that a concentration of 1,2-propanediol in the aqueous phase P1 in the range of 10 to 30% by weight results. By an appropriate recycling of water, on the one hand formation of dipropylene glycol and tripropylene glycol in step a) can be prevented and on the other hand the amount of water, which has to be separated from 1,2-propanediol by distillation, can be kept low. Membranes based on the polymers polyamide, polyether sulphone, polysulphone and polyamide-imide can be used for the nanofiltration. Suitable nanofiltration membranes are commercially available, for example, from GE Water & Process Technologies under the name DK Series, from Dow Water & Process Solutions under the name DOW FILMTEC™ NF, from Hydranautics under the names ESNA, ESP and SWC, from Toray Industries under the names TM700 and TM800, from SolSep under the name NF 010206W, and also from AMS Technologies under the names NanoPro™ A, NanoPro™ S and NanoPro™ B.

In addition to the nanofiltration or as an alternative thereto, tungstate and heteropolytungstate can be removed from the aqueous phase P1 by adsorption on a support material. For such an adsorption, preference is given to using a cationized inorganic support material described in WO 2009/133053 on page 7, line 1 to page 8, line 29. The adsorption on the support material and the recovery of tungstate and heteropolytungstate adsorbed on the support material is preferably carried out using the methods described in WO 2009/133053 and WO 2013/110419. If the adsorption is used in addition to a nanofiltration in step d), the adsorption is preferably carried out after the nanofiltration in order to keep the demand for support material low.

Nanofiltration and adsorption on a support material are preferably carried out before the hydrogenation described above, in order to avoid deactivation of the hydrogenation catalyst by tungstate or heteropolytungstate.

In a preferred embodiment of the process according to the invention, the aqueous phase P1 separated in step b) is brought into contact with liquid propene in step d) to obtain an aqueous phase P3 and an organic phase P4, the organic phase P4 is recycled into the reaction of step a) and 1,2-propanediol is separated from the aqueous phase P3. In this embodiment, preferably no separation of tungsten from the aqueous phase P1 is carried out and tungsten is separated from the aqueous phase P3, preferably by nanofiltration and/or adsorption as described above for the aqueous phase P1. The aqueous phase P1 is brought into contact with propene preferably in an additional mixed reactor with a residence time in the reactor which leads to a conversion of the hydrogen peroxide present in the aqueous phase of at least 50%, preferably at least 80%. The bringing into contact in the additional reactor is carried out preferably at a temperature of 60 to 100° C. and a pressure which is above the saturated vapour pressure of propene at the selected temperature. The aqueous phase P1 is preferably brought into contact with propene in a continuously operated reactor, particularly preferably in a loop reactor. By the use of an additional continuously operated reactor, a high conversion of hydrogen peroxide can be achieved with an overall lower reactor volume.

In this embodiment, propene is preferably supplied to the process only in step d) and gets to the reaction of step a) with the organic phase P4. If a phase transfer catalyst is used in the process which, in the presence of hydrogen peroxide, transfers more than half of the tungsten from the aqueous phase into liquid propene, the aqueous phase P1 may also be brought into contact with liquid propene in a countercurrent extraction, preferably a countercurrent extraction column, and tungsten present in the aqueous phase P1 is then recycled into step a) with the organic phase P4.

Figure 1:
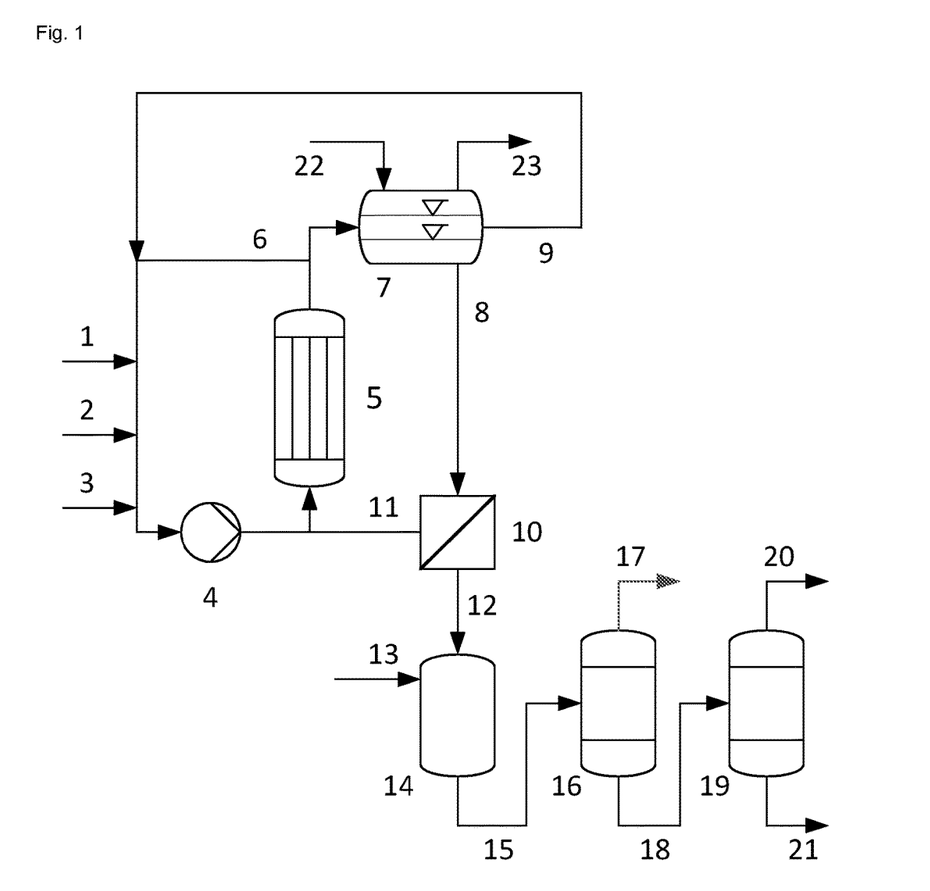

FIG. 1 shows an embodiment of the process according to the invention with a continuous reaction in step a) in a loop reactor and a nanofiltration of the aqueous phase in step d). Propene (1), hydrogen peroxide (2) and catalyst mixture (3) are fed to a reaction loop in which the liquid biphasic mixture (6), comprising an aqueous phase having a pH of at most 6 and an organic phase, is circulated through a cooled tube bundle reactor (5) using a circulating pump (4). A portion of biphasic mixture (6), which corresponds to the amount fed of propene (1), hydrogen peroxide (2) and catalyst mixture (3), is withdrawn from the reaction loop, and this portion is separated in a phase separation vessel (7) into an aqueous phase P1 (8) and an organic phase P2 (9). The organic phase P2 (9) is recycled into the reaction loop. The aqueous phase P1 (8) is separated by nanofiltration (10) into a retentate (11) enriched in heteropolytungstate and a permeate (12) depleted in heteropolytungstate. The retentate (11) is recycled into the reaction loop. The permeate (12) is converted to a hydrogenated permeate (15) in a catalytic hydrogenation (14) with hydrogen (13). The hydrogenation reduces unreacted hydrogen peroxide to water and the by-product hydroxyacetone to 1,2-propanediol. In a first distillation (16), water (17) is distilled off from the hydrogenated permeate (15) and in a second distillation (19), 1,2-propanediol (20) is distilled from the bottom product (18) of the first distillation. In the bottoms of the second distillation, water-soluble high boilers (21) arise, for example dipropylene glycol. Inert gas (22) is supplied to the gas space of the phase separation vessel (7) and an oxygen-containing gas stream (23) is withdrawn to discharge oxygen formed by decomposition of hydrogen peroxide and prevent formation of a flammable gas phase in the gas space.

Figure 2:
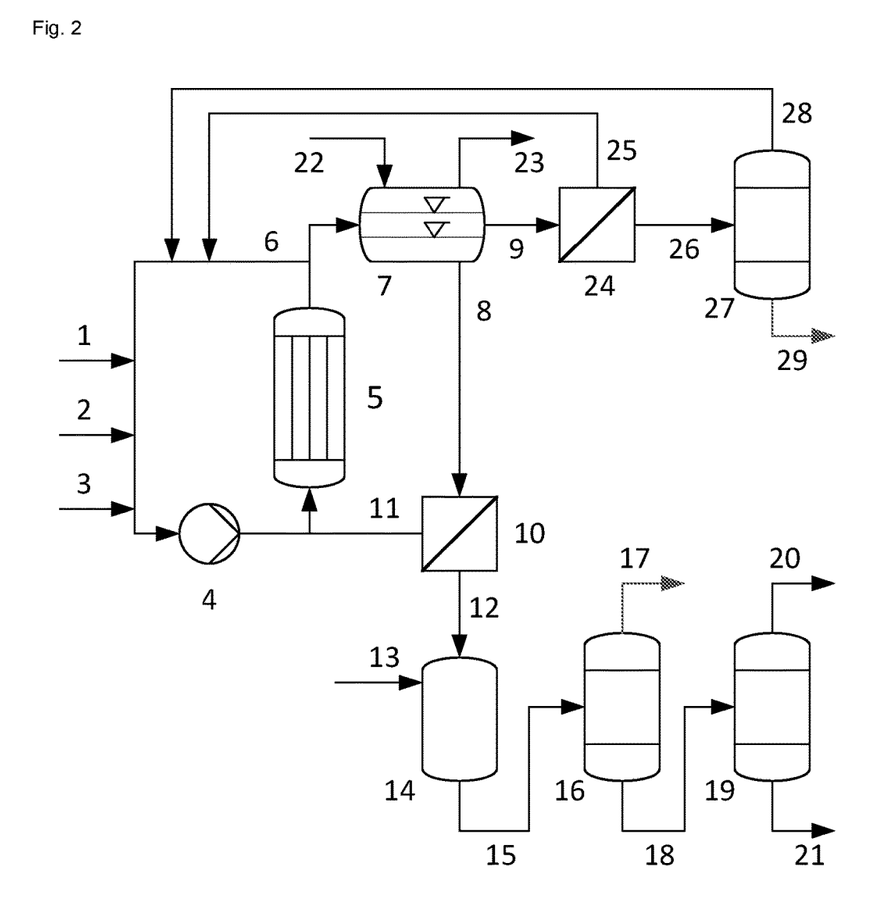

FIG. 2 shows an embodiment of the process according to the invention, which additionally comprises a nanofiltration of the organic phase with subsequent distillation in step c). The organic phase P2 (9) is separated by nanofiltration (24) into a retentate (25) enriched in heteropolytungstate and a permeate (26) depleted in heteropolytungstate. The retentate (25) is recycled into the reaction of step a). The permeate (26) is fed to a third distillation (27) in which a stream S1 (28) is obtained as overhead product, which comprises unreacted propene and propene oxide formed as intermediate. The stream S1 (28) is recycled into the reaction loop. Water-insoluble high boilers, for example degradation products of the phase transfer catalyst, are discharged with the bottom product (29) of the third distillation.

Figure 3:
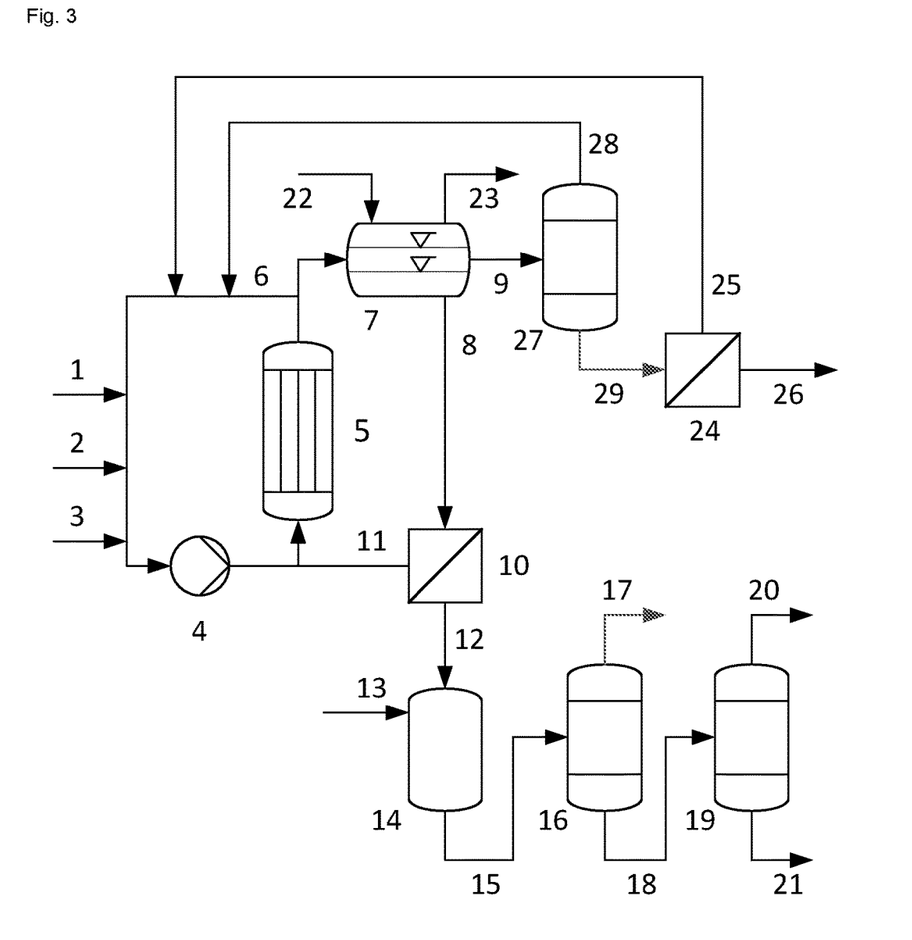

FIG. 3 shows an embodiment in which the sequence of nanofiltration and distillation is exchanged in step c) compared to the process of FIG. 2. In this embodiment, the organic phase P2 (9) is fed to the third distillation (27). The stream S1 (28) obtained as overhead product of the distillation, which comprises unreacted propene and propene oxide formed as intermediate, is recycled into the reaction loop. The bottom product (29) of the third distillation is separated by nanofiltration (24) into a retentate (25) enriched in heteropolytungstate and a permeate (26) depleted in heteropolytungstate. The retentate (25) is recycled into the reaction of step a).

Figure 4:
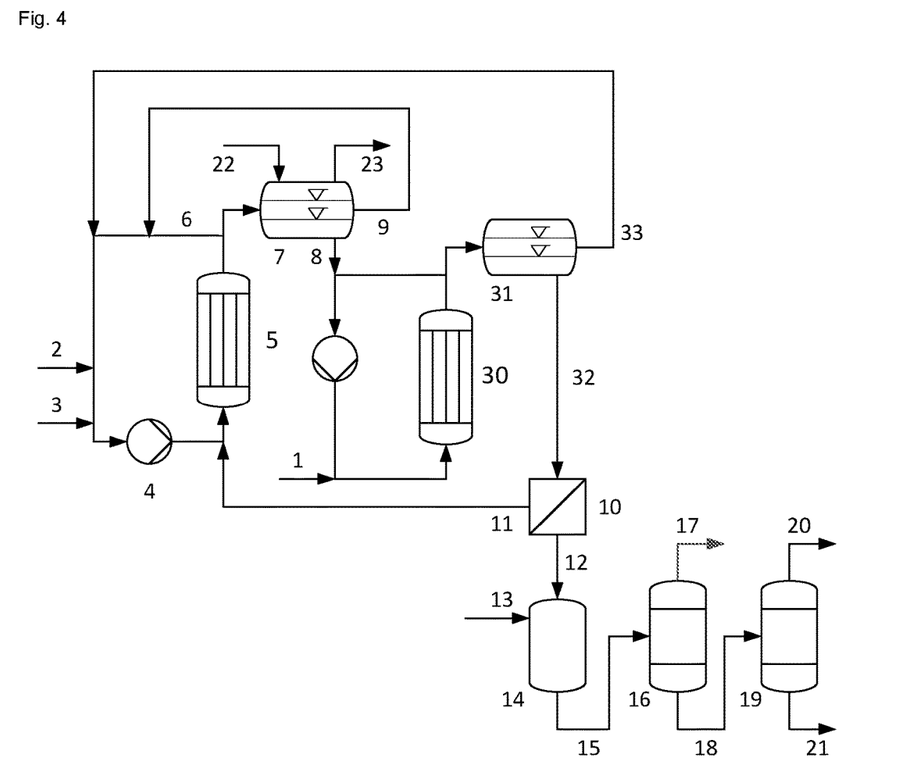

FIG. 4 shows an embodiment in which the aqueous phase P1 is once again brought into contact with propene in a reactor in step d) and 1,2-propanediol is separated from the resulting aqueous phase P3. In this embodiment, the aqueous phase P1 (8) is fed to a second reaction loop, to which the fed propene (1) is introduced in liquid from and in which the resulting liquid biphasic mixture is circulated through an additional reactor (30) with a circulating pump. A portion of biphasic mixture is withdrawn from the reaction loop, which corresponds to the amount of propene (1) and aqueous phase P1 (8) fed, and this portion is separated in a phase separation vessel (31) into an aqueous phase P3 (32) and an organic phase P4 (33). The organic phase P4 (33) is recycled into the reaction loop of the reaction of step a). 1,2-Propanediol (20) is separated from the aqueous phase P3 (32) by nanofiltration (10), catalytic hydrogenation (14), first distillation (16) and second distillation (19), as described for the aqueous phase P1 of FIG. 1. The retentate (11) is recycled into the first reaction loop.

LIST OF REFERENCE NUMBERS IN THE FIGURES 1 propene
2 hydrogen peroxide
3 catalyst mixture
4 circulating pump
5 cooled tube bundle reactor
6 biphasic mixture
7 phase separation vessel
8 aqueous phase P1
9 organic phase P2
10 nanofiltration of aqueous phase
11 retentate of nanofiltration 10
12 permeate of nanofiltration 10

13 hydrogen
14 catalytic hydrogenation
15 hydrogenated permeate 12
16 first distillation
17 water
18 bottom product of the first distillation
19 second distillation
20 1,2-propanediol
21 high boilers
22 inert gas
23 oxygen-containing gas stream
24 nanofiltration of organic phase
25 retentate of nanofiltration 24
26 permeate of nanofiltration 24
27 third distillation
28 stream comprising propene and propene oxide
29 bottom product of the third distillation
30 additional reactor
31 phase separation vessel
32 aqueous phase P3
33 organic phase P4

EXAMPLES

Example 1, Preparation of Epoxidized Soy Fatty Acid Methyl Ester 750 g of soy fatty acid methyl ester, 115 g of demineralized water, 13.8 g of REWOQUAT® 3099 (bis-(2-hydroxypropyl)-dimethylammonium methylsulphate vegetable fatty acid diester), 3.6 g of sodium tungstate dihydrate and 1.2 g of phosphoric acid were charged to a 2.5 l volume stirred vessel. At 70° C. and with stirring, 540 g of 28% by weight aqueous hydrogen peroxide solution were added over 1 h with stirring. The mixture was stirred for a further 1.5 h at 70° C., cooled to 20° C. and the epoxidized soy fatty acid methyl ester was separated by phase separation as the light phase.

Example 2, Preparation of 1,2-propanediol from Propene and Hydrogen Peroxide with Epoxidized Soy Fatty Acid Methyl Ester as Solvent The reaction of propene with hydrogen peroxide was carried out at a temperature of 78° C. and a pressure of 4.2 MPa in a 0.45 l volume loop reactor, which was operated at a circulation rate of 90 kg/h. Into the loop reactor were dosed 140 g/h of propene, 140 g/h of a 20.0% by weight aqueous solution of hydrogen peroxide, 120 g/h of an aqueous solution containing 10.0% by weight sodium tungstate dihydrate and 24.0% by weight phosphoric acid, and 240 g/h of a mixture of 8.3% by weight REWOQUAT® 3099 and 91.7% by weight epoxidized soy fatty acid methyl ester from example 1. Biphasic reaction mixture was withdrawn from the loop reactor in an amount corresponding to the amounts dosed, the mixture was decompressed to ambient pressure, whereupon dissolved propene outgassed and the phases were then separated. After 5 h operation, 301 g of reaction mixture were withdrawn within 30 min and, after the phase separation, 138 g of aqueous phase and 163 g of organic phase were obtained. The 1,2-propanediol content in the organic phase was determined by $^1$H-NMR. The hydrogen peroxide content in the aqueous phase was determined by cerimetric titration. In a sample of the aqueous phase, the hydrogen peroxide was reduced by addition of sodium sulphite and then the contents of 1,2-propanediol, hydroxyacetone, hydroxyacetone bisulphite adduct, acetaldehyde bisulphite adduct, formic acid and acetic acid were determined by $^1$H-NMR and $^{13}$C-NMR using maleic acid as external standard.

The aqueous phase comprised 60 mmol/h hydrogen peroxide, which gives a conversion of hydrogen peroxide of 93%. 26 mmol/h of 1,2-propanediol (3%) were obtained in the organic phase and, in the aqueous phase, 377 mmol/h (46%) of 1,2-propanediol, 5 mmol/h of hydroxyacetone (0.6%), 5 mmol/h of acetaldehyde, 2 mmol/h of acetic acid and 4 mmol/h of formic acid (the figures in parentheses are yields based on hydrogen peroxide used).

Example 3, Preparation of 1,2-propanediol from Propene and Hydrogen Peroxide with Epoxidized Soy Fatty Acid Methyl Ester as Solvent Example 2 was repeated, dosing 60 g/h of propene, 140 g/h of a 25.2% by weight aqueous solution of hydrogen peroxide, 220 g/h of an aqueous solution containing 1.7% by weight sodium tungstate dihydrate and 4.0% by weight phosphoric acid, and also 160 g/h of a mixture of 12.3% by weight REWOQUAT® 3099 and 87.7% by weight epoxidized soy fatty acid methyl ester into the loop reactor. After 5 h operation, 292 g of reaction mixture were withdrawn within 30 min and, after the phase separation, 204 g of aqueous phase and 88 g of organic phase were obtained.

The aqueous phase comprised 534 mmol/h hydrogen peroxide, which gives a conversion of hydrogen peroxide of 49%. 14 mmol/h of 1,2-propanediol (1%) were obtained in the organic phase and, in the aqueous phase, 263 mmol/h (25%) of 1,2-propanediol, 5 mmol/h of hydroxyacetone (0.4%), 5 mmol/h of acetaldehyde, 2 mmol/h of acetic acid and 4 mmol/h of formic acid.

Example 4, Preparation of 1,2-propanediol from Propene and Hydrogen Peroxide with Epoxidized Soy Fatty Acid Methyl Ester as Solvent Example 2 was repeated, dosing 120 g/h of propene, 140 g/h of a 25.1% by weight aqueous solution of hydrogen peroxide, 120 g/h of an aqueous solution containing 10.1% by weight sodium tungstate dihydrate and 24.0% by weight phosphoric acid, and also 160 g/h of a mixture of 8.3% by weight REWOQUAT® 3099 and 91.7% by weight epoxidized soy fatty acid methyl ester into the loop reactor. After 5 h operation, 305 g of reaction mixture were withdrawn within 30 min and, after the phase separation, 134 g of aqueous phase and 172 g of organic phase were obtained.

The aqueous phase comprised 74 mmol/h hydrogen peroxide, which gives a conversion of hydrogen peroxide of 93%. 27 mmol/h of 1,2-propanediol (3%) were obtained in the organic phase and, in the aqueous phase, 457 mmol/h (44%) of 1,2-propanediol, 8 mmol/h of hydroxyacetone (0.8%), 8 mmol/h of acetaldehyde, 2 mmol/h of acetic acid and 5 mmol/h of formic acid.

Example 5, Preparation of 1,2-propanediol from Propene and Hydrogen Peroxide with Recycling of the Organic Phase Example 2 was repeated, but using a portion of the combined organic phases from Examples 2-4 instead of epoxidized soy fatty acid methyl ester, dosing 30 g/h of propene, 93 g/h of a 29.9% by weight aqueous solution of hydrogen peroxide, 40 g/h of an aqueous solution containing 3.4% by weight sodium tungstate dihydrate and 6.9% by weight phosphoric acid, and also 160 g/h of a mixture of 1.5% by weight REWOQUAT® 3099 and 98.5% by weight of organic phases from Examples 2-4. After 5 h operation, 919 g of reaction mixture were withdrawn within 180 min and, after the phase separation, 421 g of aqueous phase and 498 g of organic phase were obtained.

The aqueous phase comprised 59 mmol/h hydrogen peroxide, which gives a conversion of hydrogen peroxide of 93%. 13 mmol/h of 1,2-propanediol (2%) were obtained in the organic phase and, in the aqueous phase, 290 mmol/h (35%) of 1,2-propanediol, 16 mmol/h of hydroxyacetone (2%), 7 mmol/h of acetaldehyde, 6 mmol/h of acetic acid and 9 mmol/h of formic acid.

Example 6, Preparation of 1,2-propanediol from Propene and Hydrogen Peroxide with Recycling of the Organic Phase Example 5 was repeated, but using a 30.4% by weight aqueous solution of hydrogen peroxide. After 5 h operation, 1095 g of reaction mixture were withdrawn within 210 min and, after the phase separation, 488 g of aqueous phase and 607 g of organic phase were obtained.

The aqueous phase comprised 62 mmol/h hydrogen peroxide, which gives a conversion of hydrogen peroxide of 93%. 14 mmol/h of 1,2-propanediol (2%) were obtained in the organic phase and, in the aqueous phase, 288 mmol/h (35%) of 1,2-propanediol, 17 mmol/h of hydroxyacetone (2%), 8 mmol/h of acetaldehyde, 6 mmol/h of acetic acid and 9 mmol/h of formic acid.

Example 7, Separation of Tungstate from the Aqueous and from the Organic Phase of the Reaction Mixture of the Epoxidation The separation of tungstate by nanofiltration was investigated in each case for the combined aqueous phases of Example 5 and 6 and the combined organic phases of Examples 5 and 6.

The nanofiltration was carried out as a dead-end filtration in a stirred filtration cell (METcell) from Evonik MET. The separation of tungstate from the aqueous phase was carried out using the GE DK membrane from GE Water & Process Technologies or the NanoPro™ B-4022 membrane from AMS Technologies. The separation of tungstate from the organic phase was carried out using the PuraMem® S 600 membrane from Evonik MET or the ONF-2 membrane from GMT Membrantechnik. Prior to determining retention capacity and permeability, the membranes for the filtration of aqueous phase were conditioned with water and aqueous phase, and the membranes for the filtration of organic phase were conditioned with organic phase, at a stirring speed of 500 min$^{-1}$ under the conditions specified in Table 1.

TABLE 1

| Membrane | Filtered medium | Pressure in MPa | Temperature in ° C. | Filtration time in min |
|---|---|---|---|---|
| GE DK | Water | 2.0 | 20 | 23 |
|  | aqueous phase | 3.0 | 20 | 137 |
| NanoPro™ B-4022 | Water | 2.0 | 20 | 40 |
|  | aqueous phase | 3.0 | 20 | 160 |
| PuraMem® S 600 | organic phase | 2.0 | 20 | 29 |
|  |  | 3.0 | 20 | 114 |
| ONF-2 | organic phase | 3.9 | 83 | 315 |

The filtration conditions for determining retention capacity and permeability are listed in Tables 2-5 and the filtration experiments were conducted at a stirring speed of 500 min$^{-1}$. The concentrations of tungsten and nitrogen in the phase used (feed), in the retentate and in the permeate and the retention capacity for tungsten and phase transfer catalyst calculated therefrom are listed in Tables 6 and 7. The retention capacity was calculated as 1−(permeate concentration)/(retentate concentration) at each given time point.

TABLE 2

Filtration of 182 g of aqueous phase with GE DK membrane

| Filtration time in min | Pressure in MPa | Temperature in ° C. | Cumulative mass of permeate in g | Permeability in kg m$^{-2}$h$^{-1}$bar$^{-1}$ |
|---|---|---|---|---|
| 0 | 3.0 | 20 | 0 |  |
| 63 | 3.0 | 20 | 18.0 | 0.11 |
| 129 | 3.0 | 20 | 36.1 | 0.11 |
| 205 | 3.0 | 20 | 54.4 | 0.10 |
| 285 | 3.0 | 20 | 72.5 | 0.10 |
| 372 | 3.0 | 20 | 89.3 | 0.09 |

TABLE 3

Filtration of 180 g of aqueous phase with NanoPro™ B-4022 membrane

| Filtration time in min | Pressure in MPa | Temperature in ° C. | Cumulative mass of permeate in g | Permeability in kg m$^{-2}$h$^{-1}$bar$^{-1}$ |
|---|---|---|---|---|
| 0 | 4.5 | 20 | 0 |  |
| 73 | 4.5 | 20 | 15.9 | 0.06 |
| 169 | 4.5 | 20 | 29.7 | 0.047 |
| 298 | 4.5 | 20 | 45.6 | 0.040 |
| 410 | 4.5 | 20 | 57.7 | 0.037 |

TABLE 4

Filtration of 197 g of organic phase with PuraMem® S 600 membrane

| Filtration time in min | Pressure in MPa | Temperature in ° C. | Cumulative mass of permeate in g | Permeability in kg m$^{-2}$h$^{-1}$bar$^{-1}$ |
|---|---|---|---|---|
| 0 | 4.0 | 21 | 0 |  |
| 385 | 4.0 | 81 | 22.1 | 0.017 |
| 745 | 4.0 | 81 | 40.4 | 0.016 |
| 1350 | 4.0 | 82 | 60.0 | 0.013 |
| 1985 | 3.9 | 80 | 75.9 | 0.011 |
| 2780 | 3.9 | 81 | 88.6 | 0.009 |

TABLE 5

Filtration of 209 g of organic phase with ONF-2 membrane

| Filtration time in min | Pressure in MPa | Temperature in ° C. | Cumulative mass of permeate in g | Permeability in kg m$^{-2}$h$^{-1}$bar$^{-1}$ |
|---|---|---|---|---|
| 0 | 4.0 | 21 | 0 |  |
| 930 | 4.0 | 82 | 22.8 | 0.007 |
| 1875 | 4.0 | 83 | 40.0 | 0.006 |
| 2940 | 3.9 | 82 | 57.5 | 0.005 |

TABLE 6

Nanofiltration of aqueous phase

| Membrane | Sample analyzed | Concentration of tungsten in ppm | Concentration of nitrogen in ppm | Tungstate retention in % | PTC retention in % |
|---|---|---|---|---|---|
| GE DK | Feed | 66 | 84 | | |
| | Retentate after 372 min | 100 | 155 | | |
| | Permeate after 372 min | n.d. | 18 | n.d. | 84 |
| NanoPro ™ B-4022 | Feed | 66 | 84 | | |
| | Retentate after 410 min | 70 | 100 | | |
| | Permeate after 410 min | 22 | 25 | 69 | 75 | n.d.: not determined

TABLE 7

Nanofiltration of organic phase

| Membrane | Sample analyzed | Concentration of tungsten in % by weight | Concentration of nitrogen in ppm | Tungstate retention in % | PTC retention in % |
|---|---|---|---|---|---|
| PuraMem ® S 600 | Feed | 2.1 | 1800 | | |
| | Retentate after 46 min | 3.8 | 2950 | | |
| | Permeate after 46 min | 0.4 | 450 | 89 | 85 |
| ONF-2 | Feed | 2.1 | 1800 | | |
| | Retentate after 49 min | 2.7 | 1850 | | |
| | Permeate after 49 min | 0.5 | 18 | 81 | 99 |

Example 8, Preparation of 1,2-Propanediol from Propene and Hydrogen Peroxide with a C10 Aromatic Compound Mixture as Solvent The reaction of propene with hydrogen peroxide was carried out at a temperature of 78° C. and a pressure of 4.2 MPa in a 0.5 l volume loop reactor, which was operated at a circulation rate of 90 kg/h. Into the loop reactor were dosed 90 g/h of propene, 140 g/h of a 20.1% by weight aqueous solution of hydrogen peroxide, 120 g/h of an aqueous solution, containing 10.1% by weight sodium tungstate dihydrate, 24.0% by weight phosphoric acid and 1.5% by weight hydrogen peroxide, whose pH had been adjusted to 1.5 with solid sodium hydroxide, and also 240 g/h of a mixture of 5.7% by weight trioctylamine and 94.3% by weight Hydrosol A 200 ND (low napthalene C10-aromatic compound mixture, DHC Solvent Chemie). Biphasic reaction mixture was withdrawn from the loop reactor in an amount corresponding to the amounts dosed, 262 g/h of aqueous phase were separated from organic phase and gas phase in a first phase separation vessel at 1.6 MPa and 301 g/h of organic phase were separated from the gas phase in a second phase separation vessel at the same pressure. 50 Nl/h of nitrogen were dosed into the second phase separation vessel, gas phase was removed via a pressure-holding valve and the oxygen content in this gas phase was determined using a paramagnetic oxygen sensor. Without pressure reduction, the propene oxide content in the organic phase was determined by GC-MS. The pH and the hydrogen peroxide content in the aqueous phase was determined by cerimetric titration. In a sample of the aqueous phase, the hydrogen peroxide was reduced by addition of sodium sulphite and then the contents of 1,2-propanediol, dipropylene glycol, hydroxyacetone, hydroxyacetone bisulphite adduct, acetaldehyde bisulphite adduct, formic acid and acetic acid were determined by $^1$H-NMR and $^{13}$C-NMR using maleic acid as external standard.

1 mmol/h of oxygen was obtained in the gas phase. The aqueous phase had a pH of 2.0 and comprised 223 mmol/h hydrogen peroxide, which gives a conversion of hydrogen peroxide of 75%. 27 mmol/h of propene oxide (3%) were obtained in the organic phase and, in the aqueous phase, 310 mmol/h (35%) of 1,2-propanediol, 16 mmol/h (2%) of dipropylene glycol, 13 mmol/h of hydroxyacetone (1.5%), 11 mmol/h of acetaldehyde, 9 mmol/h of acetic acid and 6 mmol/h of formic acid (the figures in parentheses are yields based on hydrogen peroxide used).

Example 9, Preparation of 1,2-propanediol from Propene and Hydrogen Peroxide with Recycling of the Organic Phase Example 8 was repeated, dosing into the loop reactor 90 g/h of propene, 140 g/h of a 20.3% by weight aqueous solution of hydrogen peroxide, 120 g/h of an aqueous solution, containing 1.5% by weight sodium tungstate dihydrate, 3.5% by weight phosphoric acid and 0.1% by weight of hydrogen peroxide, whose pH had been adjusted to 1.5 with solid sodium hydroxide, and also 240 g/h of a mixture of 0.6% by weight trioctylamine and 99.4% by weight of organic phase from example 8 depressurized to ambient pressure.

8 mmol/h of oxygen were obtained in the gas phase. The aqueous phase had a pH of 1.7 and comprised 124 mmol/h hydrogen peroxide, which gives a conversion of hydrogen peroxide of 85%. 25 mmol/h of propene dioxide (3%) were obtained in the organic phase and, in the aqueous phase, 438 mmol/h (52%) of 1,2-propanediol, 21 mmol/h (2.5%) of dipropylene glycol, 24 mmol/h of hydroxyacetone (3%), 11 mmol/h of acetaldehyde, 9 mmol/h of acetic acid and 12 mmol/h of formic acid.

Example 10, Preparation of 1,2-propanediol from Propene and Hydrogen Peroxide with Recycling of the Organic Phase Example 9 was repeated, using a 20.0% by weight aqueous solution of hydrogen peroxide and organic phase from example 9 depressurized to ambient pressure.

24 mmol/h of oxygen were obtained in the gas phase. The aqueous phase had a pH of 1.8 and comprised 143 mmol/h hydrogen peroxide, which gives a conversion of hydrogen peroxide of 83%. 26 mmol/h of propene dioxide (3%) were obtained in the organic phase and, in the aqueous phase, 394 mmol/h (48%) of 1,2-propanediol, 19 mmol/h (2.3%) of dipropylene glycol, 21 mmol/h of hydroxyacetone (2.5%), 12 mmol/h of acetaldehyde, 10 mmol/h of acetic acid and 6 mmol/h of formic acid.

Example 11, Preparation of 1,2-Propanediol from Propene and Hydrogen Peroxide Using a C10-Aromatic Compound Mixture as Solvent with Separation of Tungstate from the Aqueous and Organic Phase Example 10 was repeated, dosing into the loop reactor 120 g/h of propene, 140 g/h of a 20.4% by weight aqueous solution of hydrogen peroxide, 120 g/h of an aqueous solution, containing 16.1% by weight sodium tungstate dihydrate, 25.6% by weight phosphoric acid and 1.5% by weight hydrogen peroxide, whose pH had been adjusted to 1.5 with solid sodium hydroxide, and also 320 g/h of a mixture of 2.0% by weight trioctylamine and 98.0% by weight Hydrosol A 200 ND (low napthalene C10 aromatic compound mixture, DHC Solvent Chemie).

0.1 mmol/h of oxygen were obtained in the gas phase. The aqueous phase had a pH of 2.0 and comprised 58 mmol/h hydrogen peroxide, which gives a conversion of hydrogen peroxide of 94%. 17 mmol/h of propene oxide (2%) were obtained in the organic phase and, in the aqueous phase, 420 mmol/h (50%) of 1,2-propanediol, 20 mmol/h (2.4%) of dipropylene glycol, 12 mmol/h of hydroxyacetone (1%), 10 mmol/h of acetaldehyde, 6 mmol/h of acetic acid and 4 mmol/h of formic acid.

After depressurizing the reaction mixture and phase separation, the separation of tungstate by nanofiltration were investigated separately for the resulting aqueous phase and organic phase. The nanofiltration was carried out as a dead-end filtration in a stirred filtration cell (METcell) from Evonik MET. The separation of tungstate from the aqueous phase was carried out using the GE DK membrane from GE Water & Process Technologies. The separation of tungstate from the organic phase was carried out using the ONF-2 membrane from GMT Membrantechnik. Prior to determining retention capacity and permeability, the membranes for the filtration of aqueous phase were conditioned with water and aqueous phase, and the membranes for the filtration of organic phase were conditioned with organic phase, at a stirring speed of 500 min$^{-1}$ under the conditions specified in Table 8.

TABLE 8

| Membrane | Filtered medium | Pressure in MPa | Temperature in °C. | Filtration time in min |
|---|---|---|---|---|
| GE DK | Water | 3.0 | 20 | 17 |
|  | aqueous phase | 3.0 | 20 | 438 |
| ONF-2 | organic phase | 3.0 | 20 | 34 |

The filtration conditions for determining retention capacity and permeability are listed in Tables 9 and 10 and the filtration experiments were conducted at a stirring speed of 500 min$^{-1}$. The concentrations of tungsten and nitrogen in the phase used (feed), in the retentate and in the permeate and the retention capacity for tungsten and phase transfer catalyst calculated therefrom are listed in Tables 11 and 12. The retention capacity was calculated as 1−(permeate concentration)/(retentate concentration) at each given time point.

TABLE 9

Filtration of 183 g of aqueous phase with GE DK membrane

| Filtration time in min | Pressure in MPa | Temperature in °C. | Cumulative mass of permeate in g | Permeability in kg m$^{-2}$h$^{-1}$bar$^{-1}$ |
|---|---|---|---|---|
| 0 | 3.0 | 24 | 0 |  |
| 98 | 3.0 | 24 | 18.0 | 0.071 |
| 198 | 3.0 | 24 | 36.2 | 0.071 |
| 314 | 3.0 | 24 | 54.4 | 0.067 |
| 470 | 3.0 | 24 | 72.8 | 0.062 |
| 560 | 3.0 | 24 | 90.0 | 0.062 |

TABLE 10

Filtration of 200 g of organic phase with ONF-2 membrane

| Filtration time in min | Pressure in MPa | Temperature in °C. | Cumulative mass of permeate in g | Permeability in kg m$^{-2}$h$^{-1}$bar$^{-1}$ |
|---|---|---|---|---|
| 0 | 3.0 | 25 | 0 |  |
| 10 | 3.0 | 25 | 20.2 | 0.772 |
| 21 | 3.0 | 25 | 40.0 | 0.735 |
| 32 | 3.0 | 25 | 59.8 | 0.710 |
| 46 | 3.0 | 25 | 79.5 | 0.667 |
| 62 | 3.0 | 25 | 100.3 | 0.625 |

TABLE 11

Nanofiltration of aqueous phase

| Membrane | Sample analyzed | Concentration of tungsten in ppm | Concentration of nitrogen in ppm | Tungstate retention in % | PTC retention in % |
|---|---|---|---|---|---|
| GE DK | Feed | 21000 | 51 |  |  |
|  | Retentate after 560 min | 40000 | 58 |  |  |
|  | Permeate after 560 min | 2800 | 39 | 93 | 33 |

TABLE 12

Nanofiltration of organic phase

| Membrane | Sample analyzed | Concentration of tungsten in ppm | Concentration of nitrogen in ppm | Tungstate retention in % | PTC retention in % |
|---|---|---|---|---|---|
| ONF-2 | Feed | 15000 | 1650 |  |  |
|  | Retentate after 62 min | 29000 | 3300 |  |  |
|  | Permeate after 62 min | 7 | 210 | 99.998 | 94 |

The invention claimed is:
1. A process for preparing 1,2-propanediol from propene and hydrogen peroxide, comprising the steps of:
a) reacting propene with hydrogen peroxide in the presence of a catalyst mixture comprising a phase transfer catalyst and a heteropolytungstate, wherein the reaction is carried out in a biphasic liquid mixture comprising an aqueous phase having a pH of at most 6 and an organic phase;
b) separating the biphasic mixture from step a) into an aqueous phase P1 and an organic phase P2 comprising propene oxide;
c) recycling the propene oxide present in the separated organic phase P2 into the reaction of step a); and
d) separating 1,2-propanediol from the aqueous phase P1 separated in step b).
2. The process of claim 1, wherein the heteropolytungstate present in the organic phase P2 separated in step c) is recycled into the reaction of step a).
3. The process of claim 1, wherein the pH of the aqueous phase in step a) is maintained in the range of 1.0 to 3.5.
4. The process of claim 1, wherein the aqueous phase P1 is separated by nanofiltration in step d) into a retentate enriched in heteropolytungstate and a permeate depleted in heteropolytungstate, the retentate is recycled into the reaction of step a) and 1,2-propanediol is separated from the permeate.

5. The process of claim 1, wherein the reaction in step a) is carried out in the presence of at least one solvent having a boiling point of more than 100° C. and a water solubility at 20° C. of less than 250 mg/kg.

6. The process of claim 5, wherein the solvent comprises an epoxidized fatty acid methyl ester.

7. The process of claim 5, wherein the solvent comprises an alkylated aromatic hydrocarbon having 8 to 12 carbon atoms.

8. The process of claim 1, wherein the organic phase P2 separated in step b) is completely or partly recycled into the reaction of step a).

9. The process of claim 1, wherein the organic phase P2 is separated completely or partly by nanofiltration in step c) into a retentate enriched in heteropolytungstate and a permeate depleted in heteropolytungstate and the retentate enriched in heteropolytungstate is recycled into the reaction of step a).

10. The process of claim 9, wherein the organic phase P2 is separated by nanofiltration into the retentate enriched in heteropolytungstate and the permeate depleted in heteropolytungstate, a stream S1 comprising unreacted propene and propene oxide formed as an intermediate is separated by distillation from the permeate depleted in heteropolytungstate and this stream S1 is recycled into the reaction of step a).

11. The process of claim 9, wherein the organic phase P2 is separated by distillation into a stream S1 comprising unreacted propene and propene oxide formed as intermediate, and a stream S2 depleted in propene and propene oxide, the stream S2 is separated by nanofiltration into the retentate enriched in heteropolytungstate and the permeate depleted in heteropolytungstate and the stream S1 is recycled into the reaction of step a).

12. The process of claim 1, wherein in step d), prior to the separation of 1,2-propanediol, peroxides are removed by catalytic hydrogenation.

13. The process of claim 1, wherein the aqueous phase P1 separated in step b) is brought into contact with liquid propene in step d) to obtain an aqueous phase P3 and an organic phase P4, the organic phase P4 is recycled into the reaction of step a) and 1,2-propanediol is separated from the aqueous phase P3.

14. The process of claim 13, wherein propene is supplied to the process only in step d).

15. The process of claim 1, wherein propene is used in a mixture with propane.

16. The process of claim 1, wherein step a) is carried out continuously and the concentration of hydrogen peroxide in the aqueous phase is in the range of 0.1 to 5% by weight.

17. The process of claim 1, wherein step a) is carried out continuously in a loop reactor having fixed internals, and the biphasic liquid mixture is conducted through the loop reactor at a flow rate which generates a turbulent flow over the internals.

18. The process of claim 1, wherein the heteropolytungstate is a polytungstophosphate.

19. The process of claim 18, wherein the polytungstophosphate in step a) is generated in situ from phosphoric acid and sodium tungstate.

20. The process of claim 19, wherein phosphoric acid and sodium tungstate are used in a molar ratio of from 1:2 to 10:1.

21. The process of claim 1, wherein the phase transfer catalyst comprises at least one salt having a tertiary or quaternary ammonium ion of the structure $R^1R^2R^3R^4N^+$, wherein:
$R^1$ is a Y—O(C=O)$R^5$ group, wherein Y is a group $CH_2CH_2$, $CH(CH_3)CH_2$ or $CH_2CH(CH_3)$ and $R^5$ is an alkyl group or alkenyl group having 11 to 21 carbon atoms;
$R^2$ is hydrogen or an alkyl group having 1 to 4 carbon atoms; and
$R^3$ and $R^4$ are each independently $R^1$, an alkyl group having 1 to 4 carbon atoms or Y—OH.

22. The process of claim 1, wherein step b) is carried out in the presence of a gas phase and the oxygen content of this gas phase is maintained at less than 7% by volume by supplying inert gas and withdrawal of a gas stream.

* * * * *